United States Patent
Sbihli et al.

(10) Patent No.: US 9,003,880 B2
(45) Date of Patent: Apr. 14, 2015

(54) REFERENCE SPEED MEASUREMENT FOR A NON-DESTRUCTIVE TESTING SYSTEM

(71) Applicant: General Electric Company, Schenectady, NY (US)

(72) Inventors: Scott Leo Sbihli, Lexington, MA (US); Jason Howard Messinger, Andover, MA (US); Francois Xavier De Fromont, State College, PA (US); Robert Carroll Ward, Essex, CT (US)

(73) Assignee: General Electric Company, Schenectady, NY (US)

( * ) Notice: Subject to any disclaimer, the term of this patent is extended or adjusted under 35 U.S.C. 154(b) by 150 days.

(21) Appl. No.: 13/732,268

(22) Filed: Dec. 31, 2012

(65) Prior Publication Data

US 2014/0182373 A1    Jul. 3, 2014

(51) Int. Cl.
| | | |
|---|---|---|
| *G01P 3/00* | (2006.01) | |
| *G01N 29/265* | (2006.01) | |
| *G01P 1/00* | (2006.01) | |
| *G01N 27/90* | (2006.01) | |
| *G01N 29/22* | (2006.01) | |
| *G01N 29/27* | (2006.01) | |
| *G01N 29/275* | (2006.01) | |
| *G01N 29/32* | (2006.01) | |
| *G01N 21/954* | (2006.01) | |

(52) U.S. Cl.
CPC ............... *G01P 1/00* (2013.01); *G01N 27/902* (2013.01); *G01N 27/9026* (2013.01); *G01N 27/906* (2013.01); *G01N 29/225* (2013.01); *G01N 29/265* (2013.01); *G01N 29/27* (2013.01); *G01N 29/275* (2013.01); *G01N 29/32* (2013.01); *G01N 21/954* (2013.01)

(58) Field of Classification Search
USPC .................. 73/488, 489, 491, 494, 495, 620, 73/627–629, 632–635, 639
See application file for complete search history.

(56) References Cited

U.S. PATENT DOCUMENTS

| | | | |
|---|---|---|---|
| 3,835,374 | A | 9/1974 | Frost |
| 4,330,748 | A | 5/1982 | Holden |
| 5,191,285 | A | 3/1993 | Ghostine et al. |
| 5,392,652 | A * | 2/1995 | Levesque et al. ............... 73/629 |
| 5,446,378 | A * | 8/1995 | Reich et al. ................... 324/238 |
| 5,952,577 | A | 9/1999 | Passi |
| 6,317,039 | B1 | 11/2001 | Thomason |

(Continued)

FOREIGN PATENT DOCUMENTS

| | | |
|---|---|---|
| EP | 2085155 A1 | 8/2009 |
| GB | 1565049 A | 4/1980 |

OTHER PUBLICATIONS

U.S. Appl. No. 13/732,238, filed Dec. 31, 2012, Michael Christopher Domke.

(Continued)

*Primary Examiner* — Helen Kwok
(74) *Attorney, Agent, or Firm* — Fletcher Yoder P.C.

(57) ABSTRACT

A system includes a non-destructive testing (NDT) system having an NDT probe and a processor. The NDT probe includes a testing sensor and a motion sensor. The testing sensor is configured to capture sensor data from an inspection area, and the motion sensor is configured to detect a measurement speed at which the NDT probe moves relative to the inspection area. The processor is configured to determine a speed comparison between the measurement speed and a reference speed range.

20 Claims, 9 Drawing Sheets

(56) References Cited

U.S. PATENT DOCUMENTS

| | | | | |
|---|---|---|---|---|
| 6,829,959 | B2* | 12/2004 | Gifford et al. | 73/866.5 |
| 6,830,545 | B2 | 12/2004 | Bendall | |
| 8,059,882 | B2 | 11/2011 | Amidi | |
| 8,108,168 | B2 | 1/2012 | Sharp et al. | |
| 8,255,170 | B2 | 8/2012 | Kollgaard et al. | |
| 8,689,929 | B2* | 4/2014 | Sun | 181/121 |
| 2002/0198997 | A1 | 12/2002 | Linthicum et al. | |
| 2012/0271824 | A1* | 10/2012 | Goldfine et al. | 707/736 |

OTHER PUBLICATIONS

U.S. Appl. No. 13/732,252, filed Dec. 31, 2012, Kevin Andrew Coombs.
U.S. Appl. No. 13/732,261, filed Dec. 31, 2012, Eugene Schiefer.
U.S. Appl. No. 13/732,281, filed Dec. 31, 2012, Jason Howard Messinger.
U.S. Appl. No. 13/732,293, filed Dec. 31, 2012, Jason Howard Messinger.
U.S. Appl. No. 13/732,303, filed Dec. 31, 2012, Thomas Eldred Lambdin.
U.S. Appl. No. 13/732,309, filed Dec. 31, 2012, Jason Howard Messinger.
U.S. Appl. No. 13/732,272, filed Dec. 31, 2012, Jason Howard Messinger.
U.S. Appl. No. 13/732,319, filed Dec. 31, 2012, Michael Christopher Domke.
U.S. Appl. No. 13/732,327, filed Dec. 31, 2012, Michael Christopher Domke.
U.S. Appl. No. 13/747,408, filed Jan. 22, 2013, Michael Christopher Domke.
U.S. Appl. No. 13/747,435, filed Jan. 22, 2013, Jason Howard Messinger.
U.S. Appl. No. 13/747,438, filed Jan. 22, 2013, Jason Howard Messinger.
U.S. Appl. No. 13/747,457, filed Jan. 22, 2013, Jason Howard Messinger.
U.S. Appl. No. 13/747,453, filed Jan. 22, 2013, Sekhar Soorianarayanan.
U.S. Appl. No. 13/747,429, filed Jan. 22, 2013, Sekhar Soorianarayanan.
U.S. Appl. No. 13/747,464, filed Jan. 22, 2013, Sekhar Soorianarayanan.
U.S. Appl. No. 13/747,443, filed Jan. 22, 2013, Jason Howard Messinger.
U.S. Appl. No. 13/747,449, filed Jan. 22, 2013, Michael Christopher Domke.
U.S. Appl. No. 13/747,456, filed Jan. 22, 2013, Michael Christopher Domke.
U.S. Appl. No. 13/747,416, filed Jan. 22, 2013, Michael Christopher Domke.
U.S. Appl. No. 13/800,015, filed Mar. 13, 2013, Kevin Andrew Coombs.
PCT Search Report and Written Opinion issued Mar. 19, 2014 in connection with corresponding PCT Application No. PCT/US2013/074566.
Sorrel, Charlie. iControlPad Ships at Last [online], [retrieved on Mar. 21, 2013]. Retrieved from the Internet <URL: http://www.wired.com/gadgetlab/2011/11/icontrolpad-ships-at-last/>.
OmniScan MX [online]. Page 5. Olympus, 2010 [retrieved on Mar. 28, 2013]. Retrieved from the Internet: <URL: www.olympus-ims.com/en/omniscan-mx/>.
Georgeson, Gary. [online], [retrieved on Mar. 28, 2013]. http://www.meetingdata.utcdayton.com/agenda/airworthiness/2012/proceedings/presentations/P5526.pdf.
Phasor XS User's Manual [online]. General Electric: Measurement & Control Solutions. [retrieved on Mar. 28, 2013]. Retrieved from the Internet: <URL: www.ge-mcs.com/download/ultrasound/portable-flaw-detectors/Phasor%20Series/ om-phasor-en_rev10.pdf>.
USM Vision 1.2—A Total Weld Inspection Solution to Increase Productivity in New Process Pipework Fabrication [online]. General Electric: Measurement & Control. [retrieved on Mar. 28, 2013]. Retrieved from the Internet: <URL: www.ge-mcs.com/download/ultrasound/portable-flaw-detectors/usm-vision/GEIT-USMVision-20058EN_LR.pdf>.

* cited by examiner

REFERENCE SPEED MEASUREMENT FOR A NON-DESTRUCTIVE TESTING SYSTEM

BACKGROUND

The present disclosure relates to non-destructive testing (NDT) systems, and particularly to systems and methods for a reference speed measurement for a non-destructive testing system.

Certain equipment and facilities, such as power generation equipment and facilities, oil and gas equipment and facilities, aircraft equipment and facilities, manufacturing equipment and facilities, and the like, include a plurality of interrelated systems, and processes. For example, power generation plants may include turbine systems and processes for operating and maintaining the turbine systems. Likewise, oil and gas operations may include carbonaceous fuel retrieval systems and processing equipment interconnected via pipelines. Similarly, aircraft systems may include airplanes and maintenance hangars useful in maintaining airworthiness and providing for maintenance support. During equipment operations, the equipment may degrade, encounter undesired conditions such as corrosion, wear and tear, and so on, potentially affecting overall equipment effectiveness. Certain inspection techniques, such as non-destructive inspection techniques or non-destructive testing (NDT) techniques, may be used to detect undesired equipment conditions.

In a conventional NDT system, data may be shared with other NDT operators or personnel using portable memory devices, paper, of through the telephone. As such, the amount of time to share data between NDT personnel may depend largely on the speed at which the physical portable memory device is physically dispatched to its target. Accordingly, it would be beneficial to improve the data sharing capabilities of the NDT system, for example, to more efficiently test and inspect a variety of systems and equipment.

NDT probes of NDT systems receive signals used to detect undesired equipment conditions. An operator may manually move the NDT probe over an inspection area to inspect a workpiece. Unfortunately, the signals received may be affected by the position and orientation of the NDT probe. Additionally, the speed at which the NDT probe is moved affects the probability of detection and productivity of the operator.

BRIEF DESCRIPTION

Certain embodiments commensurate in scope with the originally claimed invention are summarized below. These embodiments are not intended to limit the scope of the claimed invention, but rather these embodiments are intended only to provide a brief summary of possible forms of the invention. Indeed, the invention may encompass a variety of forms that may be similar to or different from the embodiments set forth below.

In a first embodiment, a system includes a non-destructive testing (NDT) system having an NDT probe and a processor. The NDT probe includes a testing sensor and a motion sensor. The testing sensor is configured to capture sensor data from an inspection area, and the motion sensor is configured to detect a measurement speed at which the NDT probe moves relative to the inspection area. The processor is configured to determine a speed comparison between the measurement speed and a reference speed range.

In a second embodiment, a non-transitory computer readable medium includes instructions configured to capture sensor data from an inspection area, by using a non-destructive testing (NDT) probe, and to determine a measurement speed of the NDT probe and a measurement angle of the NDT probe relative to the inspection area. The instructions are further configured to determine a speed comparison between the measurement speed and a reference speed range, to determine an angle comparison between the measurement angle and a reference angle range, and to display a first graphical representation of the speed comparison and a second graphical representation of the angle comparison on a display screen.

In a third embodiment, a method includes receiving probe data from a non-destructive testing (NDT) device, wherein the probe data includes sensor data and motion data that correspond to a sample time. The method also includes comparing the motion data to one or more motion reference ranges, notifying an operator if the motion data of the sample time is outside the one or more motion reference ranges, and recording the sensor data of the sample time if the motion data of the sample time is within the one or more motion reference ranges.

BRIEF DESCRIPTION OF THE DRAWINGS

These and other features, aspects, and advantages of the present invention will become better understood when the following detailed description is read with reference to the accompanying drawings in which like characters represent like parts throughout the drawings, wherein.

DETAILED DESCRIPTION

Figure 1:
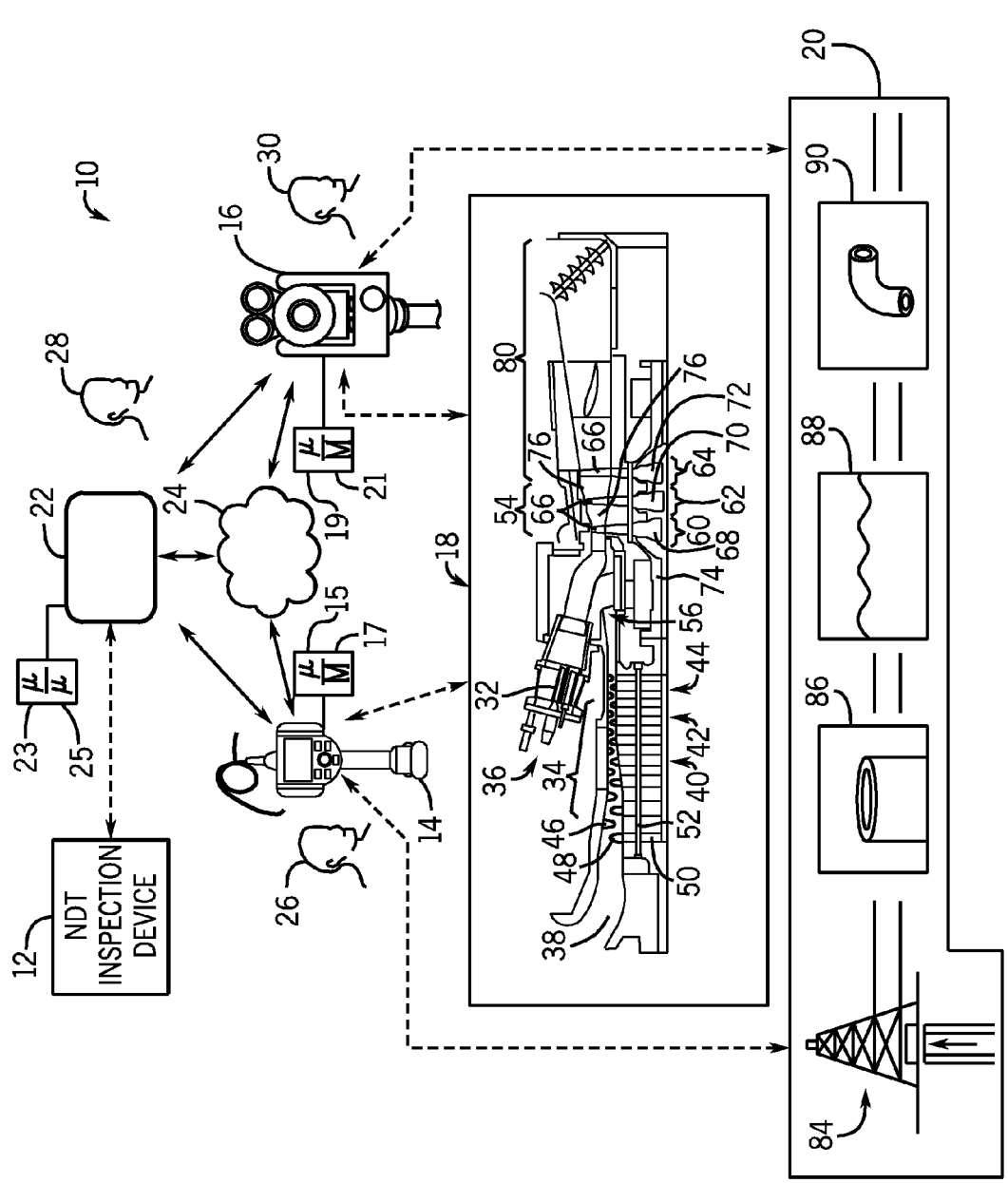
FIG. 1 is a block diagram illustrating an embodiment of a distributed non-destructive testing (NDT) system, including a mobile device.

One or more specific embodiments will be described below. In an effort to provide a concise description of these embodiments, not all features of an actual implementation are described in the specification. It should be appreciated that in the development of any such actual implementation, as in any engineering or design project, numerous implementation-specific decisions must be made to achieve the developers' specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

When introducing elements of various embodiments of the present invention, the articles "a," "an," "the," and "said" are intended to mean that there are one or more of the elements. The terms "comprising," "including," and "having" are intended to be inclusive and mean that there may be additional elements other than the listed elements.

Embodiments of the present disclosure may apply to a variety of inspection and testing techniques, including non-destructive testing (NDT) or inspection systems. In the NDT system, certain techniques such as borescopic inspection, weld inspection, remote visual inspections, x-ray inspection, ultrasonic inspection, eddy current inspection, and the like, may be used to analyze and detect a variety of conditions, including but not limited to corrosion, equipment wear and tear, cracking, leaks, and so on. The techniques described herein provide for improved NDT systems suitable for borescopic inspection, remote visual inspections, x-ray inspection, ultrasonic inspection, and/or eddy current inspection, enabling enhanced data gathering, data analysis, inspection/testing processes, and NDT collaboration techniques.

The improved NDT systems described herein may include inspection equipment using wireless conduits suitable for communicatively coupling the inspection equipment to mobile devices, such as tablets, smart phones, and augmented reality eyeglasses; to computing devices, such as notebooks, laptops, workstations, personal computers; and to "cloud" computing systems, such as cloud-based NDT ecosystems, cloud analytics, cloud-based collaboration and workflow systems, distributed computing systems, expert systems and/or knowledge-based systems. Indeed, the techniques described herein may provide for enhanced NDT data gathering, analysis, and data distribution, thus improving the detection of undesired conditions, enhancing maintenance activities, and increasing returns on investment (ROI) of facilities and equipment.

In one embodiment, a tablet may be communicatively coupled to the NDT inspection device (e.g., borescope, transportable pan-tilt-zoom camera, eddy current device, x-ray inspection device, ultrasonic inspection device), such as a MENTOR™ NDT inspection device, available from General Electric, Co., of Schenectady, N.Y., and used to provide, for example, enhanced wireless display capabilities, remote control, data analytics and/or data communications to the NDT inspection device. While other mobile devices may be used, the use of the tablet is apt, however, insofar as the tablet may provide for a larger, higher resolution display, more powerful processing cores, an increased memory, and improved battery life. Accordingly, the tablet may address certain issues, such as providing for improved visualization of data, improving the manipulatory control of the inspection device, and extending collaborative sharing to a plurality of external systems and entities.

Keeping the foregoing in mind, the present disclosure is directed towards obtaining motion data from an NDT probe of the NDT system, and using the motion data to filter the sensor data from the NDT probe. Generally, sensor data obtained from moving the sensor with a steady speed and desired orientation provides consistent inspection results. Obtaining motion data of the NDT probe enables the NDT system to provide feedback to the probe operator to adjust the motion of the NDT probe, and enables the NDT system to filter out some sensor data from inclusion in a recorded data set.

By way of introduction, and turning now to FIG. 1, the figure is a block diagram of an embodiment of distributed NDT system 10. In the depicted embodiment, the distributed NDT system 10 may include one or more NDT inspection devices 12. The NDT inspection devices 12 may be divided into at least two categories. In one category, depicted in FIG. 1, the NDT inspection devices 12 may include devices suitable for visually inspecting a variety of equipment and environments. In another category, described in more detail with respect to FIG. 2 below, the NDT devices 12 may include devices providing for alternatives to visual inspection modalities, such as x-ray inspection modalities, eddy current inspection modalities, and/or ultrasonic inspection modalities.

In the depicted first example category of FIG. 1, the NDT inspection devices 12 may include a borescope 14 having one or more processors 15 and a memory 17, and a transportable pan-tilt-zoom (PTZ) camera 16 having one or more processors 19 and a memory 21. In this first category of visual inspection devices, the borescope 14 and PTZ camera 16 may be used to inspect, for example, a turbo machinery 18, and a facility or site 20. As illustrated, the borescope 14 and the PTZ camera 16 may be communicatively coupled to a mobile device 22 also having one or more processors 23 and a memory 25. The mobile device 22 may include, for example, a tablet, a cell phone (e.g., smart phone), a notebook, a laptop, or any other mobile computing device. The use of a tablet, however, is apt insofar as the tablet provides for a good balance between screen size, weight, computing power, and battery life. Accordingly, in one embodiment, the mobile device 22 may be the tablet mentioned above, that provides for touchscreen input. The mobile device 22 may be communicatively coupled to the NDT inspection devices 12, such as the borescope 14 and/or the PTZ camera 16, through a variety of wireless or wired conduits. For example, the wireless conduits may include WiFi (e.g., Institute of Electrical and Electronics Engineers [IEEE] 802.11X), cellular conduits (e.g., high speed packet access [HSPA], HSPA+, long term evolution [LTE], WiMax), near field communications (NFC), Bluetooth, personal area networks (PANs), and the like. The wireless conduits may use a variety of communication protocols, such as TCP/IP, UDP, SCTP, socket layers, and so on. In certain embodiments, the wireless or wired conduits may include secure layers, such as secure socket layers (SSL), virtual private network (VPN) layers, encrypted layers, challenge key authentication layers, token authentication layers, and so on. Wired conduits may include proprietary cabling, RJ45 cabling, co-axial cables, fiber optic cables, and so on.

Additionally or alternatively, the mobile device 22 may be communicatively coupled to the NDT inspection devices 12, such as the borescope 14 and/or the PTZ camera 16, through the "cloud" 24. Indeed, the mobile device 22 may use the cloud 24 computing and communications techniques (e.g., cloud-computing network), including but not limited to HTTP, HTTPS, TCP/IP, service oriented architecture (SOA) protocols (e.g., simple object access protocol [SOAP], web services description languages (WSDLs)) to interface with the NDT inspection devices 12 from any geographic location, including geographic locations remote from the physical location about to undergo inspection. Further, in one embodiment, the mobile device 22 may provide "hot spot" functionality in which mobile device 22 may provide wireless access point (WAP) functionality suitable for connecting the NDT inspection devices 12 to other systems in the cloud 24, or connected to the cloud 24, such as a computing system 29 (e.g., computer, laptop, virtual machine(s) [VM], desktop, workstation). Accordingly, collaboration may be enhanced by providing for multi-party workflows, data gathering, and data analysis.

For example, a borescope operator 26 may physically manipulate the borescope 14 at one location, while a mobile device operator 28 may use the mobile device 22 to interface with and physically manipulate the borescope 14 at a second location through remote control techniques. The second location may be proximate to the first location, or geographically distant from the first location. Likewise, a camera operator 30 may physically operate the PTZ camera 16 at a third location, and the mobile device operator 28 may remote control PTZ camera 16 at a fourth location by using the mobile device 22. The fourth location may be proximate to the third location, or geographically distant from the third location. Any and all control actions performed by the operators 26 and 30 may be additionally performed by the operator 28 through the mobile device 22. Additionally, the operator 28 may communicate with the operators 26 and/or 30 by using the devices 14, 16, and 22 through techniques such as voice over IP (VOIP), virtual whiteboarding, text messages, and the like. By providing for remote collaboration techniques between the operator 28 operator 26, and operator 30, the techniques described herein may provide for enhanced workflows and increase resource efficiencies. Indeed, nondestructive testing processes may leverage the communicative coupling of the cloud 24 with the mobile device 22, the NDT inspection devices 12, and external systems coupled to the cloud 24.

In one mode of operation, the mobile device 22 may be operated by the borescope operator 26 and/or the camera operator 30 to leverage, for example, a larger screen display, more powerful data processing, as well as a variety of interface techniques provided by the mobile device 22, as described in more detail below. Indeed, the mobile device 22 may be operated alongside or in tandem with the devices 14 and 16 by the respective operators 26 and 30. This enhanced flexibility provides for better utilization of resources, including human resources, and improved inspection results.

Whether controlled by the operator 28, 26, and/or 30, the borescope 14 and/or PTZ camera 16 may be used to visually inspect a wide variety of equipment and facilities. For example, the borescope 14 may be inserted into a plurality of borescope ports and other locations of the turbomachinery 18, to provide for illumination and visual observations of a number of components of the turbomachinery 18. In the depicted embodiment, the turbo machinery 18 is illustrated as a gas turbine suitable for converting carbonaceous fuel into mechanical power. However, other equipment types may be inspected, including compressors, pumps, turbo expanders, wind turbines, hydroturbines, industrial equipment, and/or residential equipment. The turbomachinery 18 (e.g., gas turbine) may include a variety of components that may be inspected by the NDT inspection devices 12 described herein.

With the foregoing in mind, it may be beneficial to discuss certain turbomachinery 18 components that may be inspected by using the embodiments disclosed herein. For example, certain components of the turbomachinery 18 depicted in FIG. 1, may be inspected for corrosion, erosion, cracking, leaks, weld inspection, and so on. Mechanical systems, such as the turbomachinery 18, experience mechanical and thermal stresses during operating conditions, which may require periodic inspection of certain components. During operations of the turbomachinery 18, a fuel such as natural gas or syngas, may be routed to the turbomachinery 18 through one or more fuel nozzles 32 into a combustor 36. Air may enter the turbomachinery 18 through an air intake section 38 and may be compressed by a compressor 34. The compressor 34 may include a series of stages 40, 42, and 44 that compress the air. Each stage may include one or more sets of stationary vanes 46 and blades 48 that rotate to progressively increase the pressure to provide compressed air. The blades 48 may be attached to rotating wheels 50 connected to a shaft 52. The compressed discharge air from the compressor 34 may exit the compressor 34 through a diffuser section 56 and may be directed into the combustor 36 to mix with the fuel. For example, the fuel nozzles 32 may inject a fuel-air mixture into the combustor 36 in a suitable ratio for optimal combustion, emissions, fuel consumption, and power output. In certain embodiments, the turbomachinery 18 may include multiple combustors 36 disposed in an annular arrangement. Each combustor 36 may direct hot combustion gases into a turbine 54.

As depicted, the turbine 54 includes three separate stages 60, 62, and 64 surrounded by a casing 76. Each stage 60, 62, and 64 includes a set of blades or buckets 66 coupled to a respective rotor wheel 68, 70, and 72, which are attached to a shaft 74. As the hot combustion gases cause rotation of turbine blades 66, the shaft 74 rotates to drive the compressor 34 and any other suitable load, such as an electrical generator. Eventually, the turbomachinery 18 diffuses and exhausts the combustion gases through an exhaust section 80. Turbine components, such as the nozzles 32, intake 38, compressor 34, vanes 46, blades 48, wheels 50 shaft 52, diffuser 56, stages 60, 62, and 64, blades 66, shaft 74, casing 76, and exhaust 80, may use the disclosed embodiments, such as the NDT inspection devices 12, to inspect and maintain said components.

Additionally, or alternatively, the PTZ camera 16 may be disposed at various locations around or inside of the turbo machinery 18, and used to procure visual observations of these locations. The PTZ camera 16 may additionally include one or more lights suitable for illuminating desired locations, and may further include zoom, pan and tilt techniques described in more detail below with respect to FIG. 4, useful for deriving observations around in a variety of difficult to reach areas. The borescope 14 and/or the camera 16 may be additionally used to inspect the facilities 20, such as an oil and gas facility 20. Various equipment such as oil and gas equipment 84, may be inspected visually by using the borescope 14 and/or the PTZ camera 16. Advantageously, locations such as the interior of pipes or conduits 86, underwater (or underfluid) locations 88, and difficult to observe locations such as locations having curves or bends 90, may be visually inspected by using the mobile device 22 through the borescope 14 and/or PTZ camera 16. Accordingly, the mobile device operator 28 may more safely and efficiently inspect the equipment 18, 84 and locations 86, 88, and 90, and share observations in real-time or near real-time with location geographically distant from the inspection areas. It is to be understood that other NDT inspection devices 12 may be use the embodiments described herein, such as fiberscopes (e.g., articulating fiberscope, non-articulating fiberscope), and remotely operated vehicles (ROVs), including robotic pipe inspectors and robotic crawlers.

Figure 2:
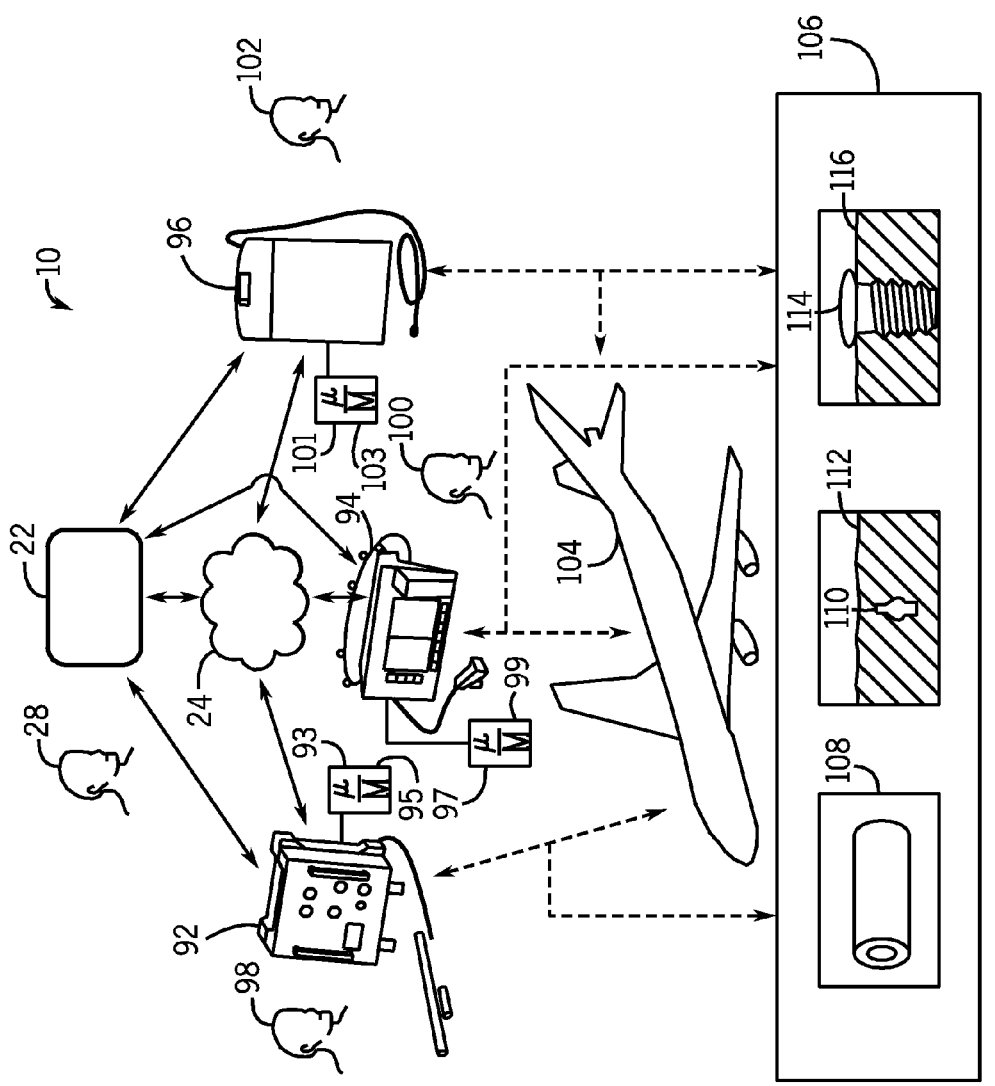
FIG. 2 is a block diagram illustrating further details of an embodiment of the distributed NDT system of FIG. 1.

Turning now to FIG. 2, the figure is a block diagram of an embodiment of the distributed NDT system 10 depicting the second category of NDT inspection devices 12 that may be able to provide for alternative inspection data to visual inspection data. For example, the second category of NDT inspection devices 12 may include an eddy current inspection device 92, an ultrasonic inspection device, such as an ultrasonic flaw detector 94, and an x-ray inspection device, such a digital radiography device 96. The eddy current inspection device 92 may include one or more processors 93 and a memory 95. Likewise, the ultrasonic flaw detector 94 may include one or more processors 97 and a memory 104. Similarly, the digital radiography device 96 may include one or more processors 101 and a memory 103. In operations, the eddy current inspection device 92 may be operated by an eddy current operator 98, the ultrasonic flaw detector 94 may be operated by an ultrasonic device operator 100, and the digital radiography device 96 may be operated by a radiography operator 102.

As depicted, the eddy current inspection device 92, the ultrasonic flaw detector 94, and the digital radiography inspection device 96, may be communicatively coupled to the mobile device 22 by using wired or wireless conduits, including the conduits mentioned above with respect to FIG. 1. Additionally, or alternatively, the devices 92, 94, and 96 may be coupled to the mobile device 22 by using the cloud 24, for example the borescope 14 may be connected to a cellular "hotspot," and use the hotspot to connect to one or more experts in borescopic inspection and analsysis. Accordingly, the mobile device operator 28 may remotely control various aspects of operations of the devices 92, 94, and 96 by using the mobile device 22, and may collaborate with the operators 98, 100, and 102 through voice (e.g., voice over IP [VOIP]), data sharing (e.g., whiteboarding), providing data analytics, expert support and the like, as described in more detail herein.

Accordingly, it may be possible to enhance the visual observation of various equipment, such as an aircraft system 104 and facilities 106, with x-ray observation modalities, ultrasonic observation modalities, and/or eddy current observation modalities. For example, the interior and the walls of pipes 108 may be inspected for corrosion and/or erosion. Likewise, obstructions or undesired growth inside of the pipes 108 may be detected by using the devices 92, 94, and/or 96. Similarly, fissures or cracks 110 disposed inside of certain ferrous or non-ferrous material 112 may be observed. Additionally, the disposition and viability of parts 114 inserted inside of a component 116 may be verified. Indeed, by using the techniques described herein, improved inspection of equipment and components 104, 108, 112 and 116 may be provided. For example, the mobile device 22 may be used to interface with and provide remote control of the devices 14, 16, 92, 94, and 96.

Figure 3:
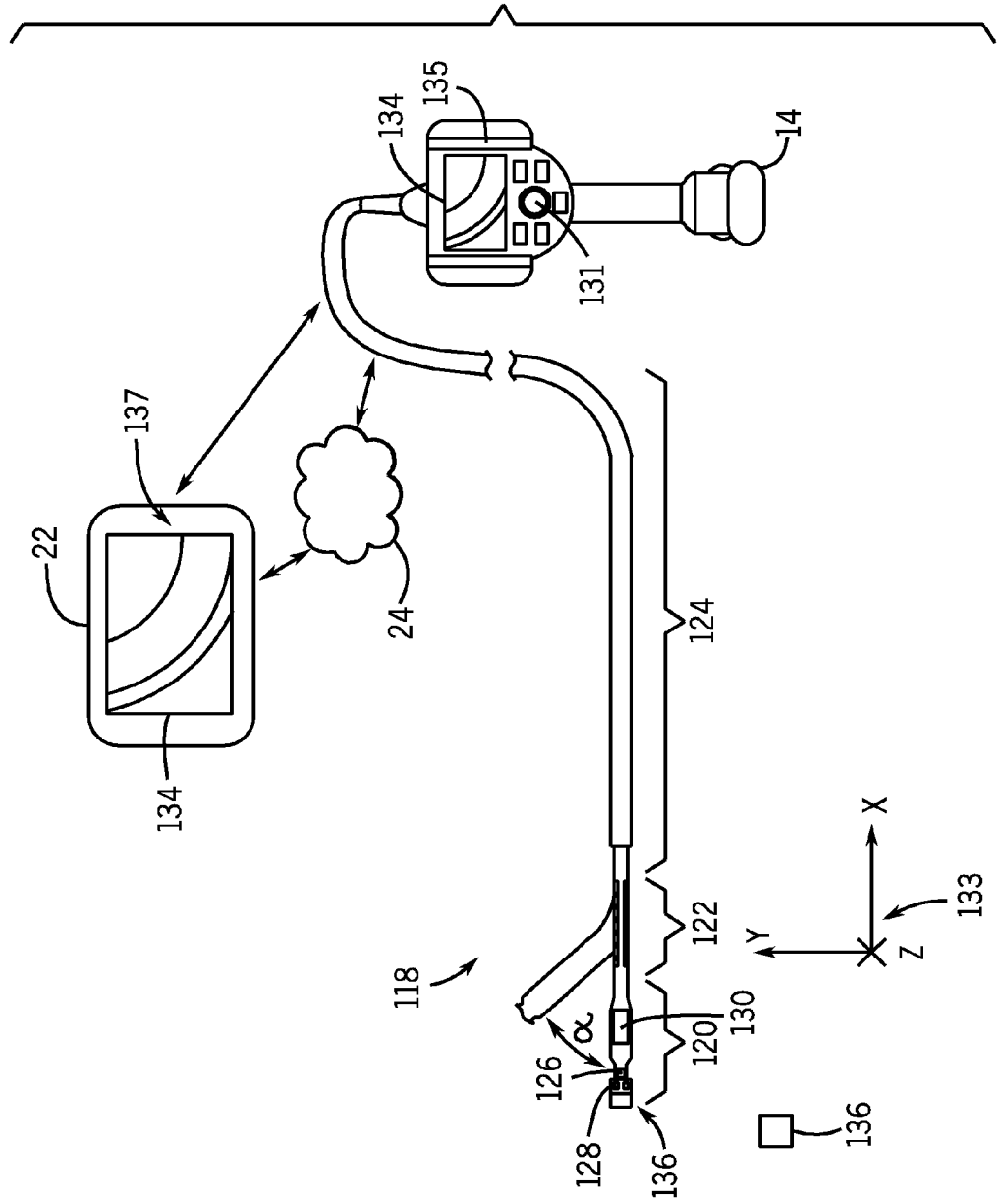
FIG. 3 is a front view illustrating an embodiment of a borescope system 14 communicatively coupled to the mobile device of FIG. 1 and a "cloud;"

FIG. 3 is a front view of the borescope 14 coupled to the mobile device 22 and the cloud 24. Accordingly, the boresecope 14 may provide data to any number of devices connected to the cloud 24 or inside the cloud 24. As mentioned above, the mobile device 22 may be used to receive data from the borescope 14, to remote control the borescope 14, or a combination thereof. Indeed, the techniques described herein enable, for example, the communication of a variety of data from the borescope 14 to the mobile device 22, including but not limited to images, video, and sensor measurements, such as temperature, pressure, flow, clearance (e.g., measurement between a stationary component and a rotary component), and distance measurements. Likewise, the mobile device 22 may communicate control instructions, reprogramming instructions, configuration instructions, and the like, as described in more detail below.

As depicted the borescope 14, includes an insertion tube 118 suitable for insertion into a variety of location, such as inside of the turbomachinery 18, equipment 84, pipes or conduits 86, underwater locations 88, curves or bends 90, varies locations inside or outside of the aircraft system 104, the interior of pipe 108, and so on. The insertion tube 118 may include a head end section 120, an articulating section 122, and a conduit section 124. In the depicted embodiment, the head end section 120 may include a camera 126, one or more lights 128 (e.g., LEDs), and sensors 130. As mentioned above, the borescope's camera 126 may provide images and video suitable for inspection. The lights 128 may be used to provide for illumination when the head end 120 is disposed in locations having low light or no light.

During use, the articulating section 122 may be controlled, for example, by the mobile device 22 and/or a physical joy stick 131 disposed on the borescope 14. The articulating sections 122 may steer or "bend" in various dimensions. For example, the articulation section 122 may enable movement of the head end 120 in an X-Y plane X-Z plane and/or Y-Z plane of the depicted XYZ axes 133. Indeed, the physical joystick 131 and/or the mobile device 22 may both be used alone or in combination, to provide control actions suitable for disposing the head end 120 at a variety of angles, such as the depicted angle α. In this manner, the borescope head end 120 may be positioned to visually inspect desired locations. The camera 126 may then capture, for example, a video 134, which may be displayed in a screen 135 of the borescope 14 and a screen 137 of the mobile device 22, and may be recorded by the borescope 14 and/or the mobile device 22. In one embodiment, the screens 135 and 137 may be multi-touchscreens using capacitance techniques, resistive techniques, infrared grid techniques, and the like, to detect the touch of a stylus and/or one or more human fingers. Additionally or alternatively, images and the video 134 may be transmitted into the cloud 24.

Other data, including but not limited to sensor 130 data, may additionally be communicated and/or recorded by the borescope 14. The sensor 130 data may include temperature data, distance data, clearance data (e.g., distance between a rotating and a stationary component), flow data, and so on. In certain embodiments, the borescope 14 may include a plurality of replacement tips 136. For example, the replacement tips 136 may include retrieval tips such as snares, magnetic tips, gripper tips, and the like. The replacement tips 136 may additionally include cleaning and obstruction removal tools, such as wire brushes, wire cutters, and the like. The tips 136 may additionally include tips having differing optical characteristics, such as focal length, stereoscopic views, 3-dimensional (3D) phase views, shadow views, and so on. Additionally or alternatively, the head end 120 may include a removable and replaceable head end 120. Accordingly, a plurality of head ends 120 may be provided at a variety of diameters, and the insertion tube 118 maybe disposed in a number of locations having openings from approximately one millimeter to ten millimeters or more. Indeed, a wide variety of equipment and facilities may be inspected, and the data may be shared through the mobile device 22 and/or the cloud 24.

Figure 4:
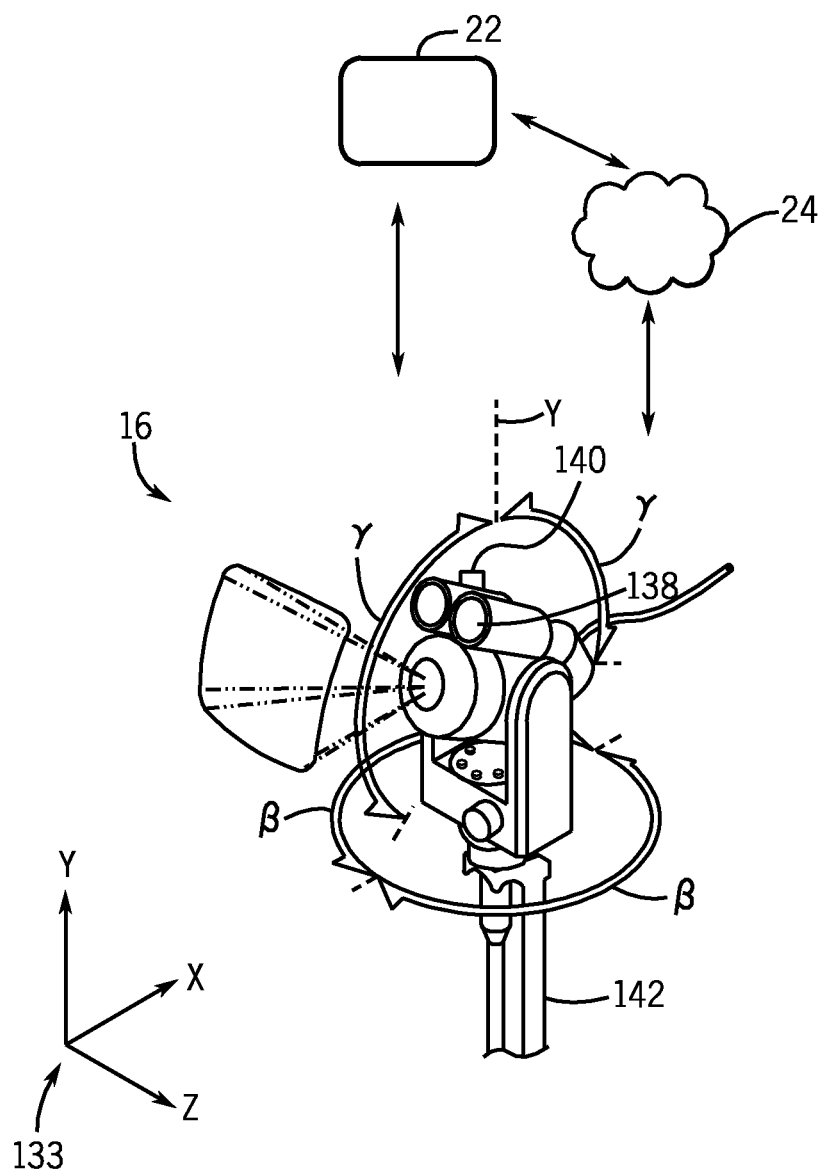
FIG. 4 is an illustration of an embodiment of a pan-tilt-zoom (PTZ) camera system communicatively coupled to the mobile device of FIG. 1.

FIG. 4 is a perspective view of an embodiment of the transportable PTZ camera 16 communicatively coupled to the mobile device 22 and to the cloud 24. As mentioned above, the mobile device 22 and/or the cloud 24 may remotely manipulate the PTZ camera 16 to position the PTZ camera 16 to view desired equipment and locations. In the depicted example, the PTZ camera 16 may be tilted and rotated about the Y-axis. For example, the PTZ camera 16 may be rotated at an angle β between approximately 0° to 180°, 0° to 270°, 0° to 360°, or more about the Y-axis. Likewise, the PTZ camera 16 may be tilted, for example, about the Y-X plane at an angle γ of approximately 0° to 100°, 0° to 120°, 0° to 150°, or more with respect to the Y-Axis. Lights 138 may be similarly controlled, for example, to active or deactivate, and to increase or decrease a level of illumination (e.g., lux) to a desired value. Sensors 140, such as a laser rangefinder, may also be mounted onto the PTZ camera 16, suitable for measuring distance to certain objects. Other sensors 140 may be used, including long-range temperature sensors (e.g., infrared temperature sensors), pressure sensors, flow sensors, clearance sensors, and so on.

The PTZ camera 16 may be transported to a desired location, for example, by using a shaft 142. The shaft 142 enables the camera operator 30 to move the camera and to position the camera, for example, inside of locations 86, 108, underwater 88, into hazardous (e.g., hazmat) locations, and so on. Additionally, the shaft 142 may be used to more permanently secure the PTZ camera 16 by mounting the shaft 142 onto a permanent or semi-permanent mount. In this manner, the PTZ camera 16 may be transported and/or secured at a desired location. The PTZ camera 16 may then transmit, for example by using wireless techniques, image data, video data, sensor 140 data, and the like, to the mobile device 22 and/or cloud 24. Accordingly, data received from the PTZ camera 16 may be remotely analyzed and used to determine the condition and suitability of operations for desired equipment and facilities. Indeed, the techniques described herein may provide for a comprehensive inspection and maintenance process suitable for planning, inspecting, analyzing, and/or sharing a variety of data by using the aforementioned devices 12, 14, 16, 22, 92, 94, 96, and the cloud 24, as described in more detail below with respect to FIG. 5.

Figure 5:
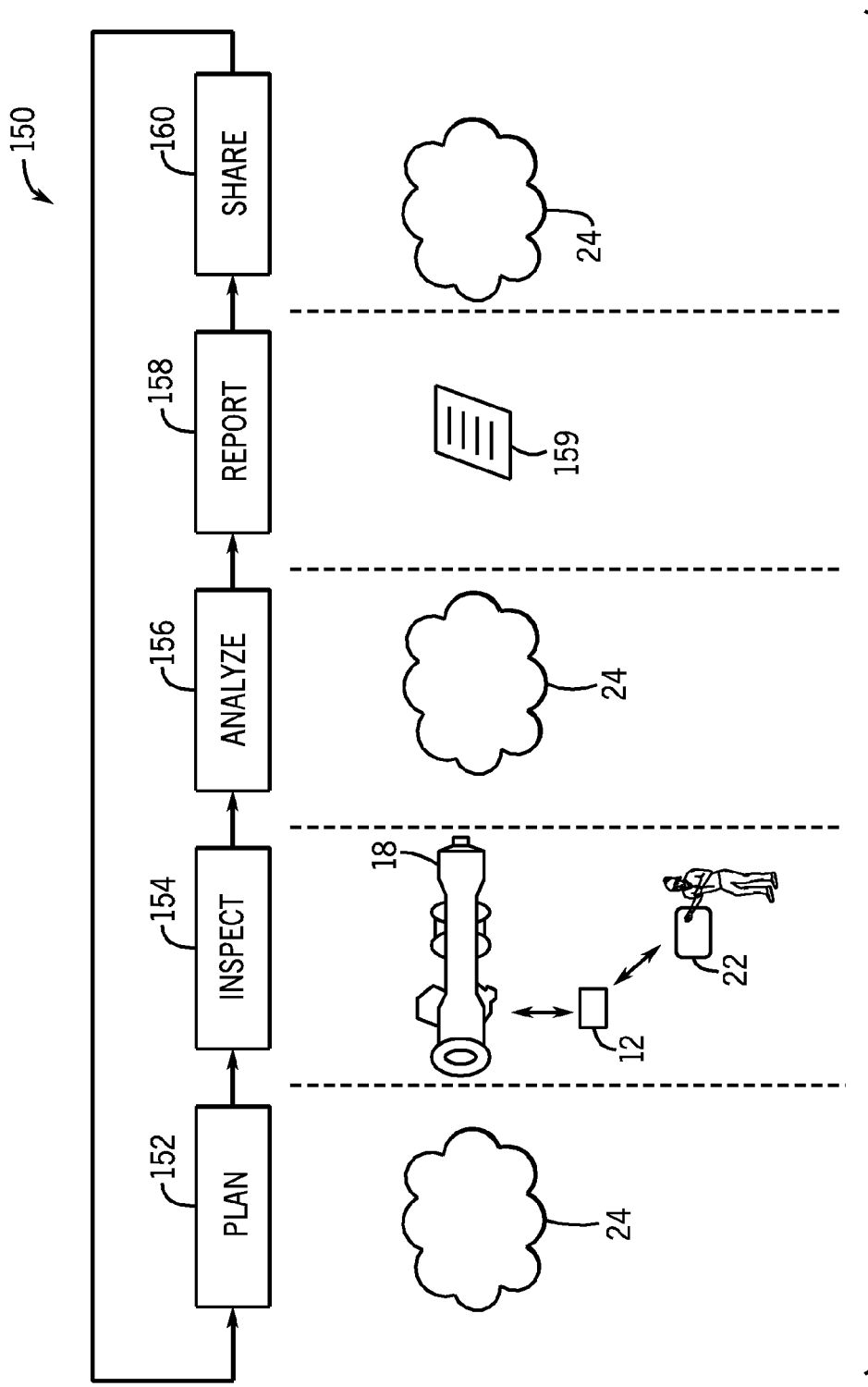
FIG. 5 is a flowchart illustrating an embodiment of a process useful in using the distributed NDT system for planning, inspecting, analyzing, reporting, and sharing of data, such as inspection data.

FIG. 5 is a flowchart of an embodiment of a process 150 suitable for planning, inspecting, analyzing, and/or sharing a variety of data by using the aforementioned devices 12, 14, 16, 22, 92, 94, 96, and the cloud 24. Indeed, the techniques described herein may use the devices 12, 14, 16, 22, 92, 94, 96 to enable processes, such as the depicted process 150, to more efficiently support and maintain a variety of equipment. In certain embodiments, the process 150 or portions of the process 150 may be included in non-transitory computer-readable media stored in memory, such as the memory 17, 21, 25, 95, 99, 103 and executable by one or more processors, such as the processors 15, 19, 23, 93, 97, 101.

In one example, the process 150 may plan (block 152) for inspection and maintenance activities. Data acquired by using the devices 12, 14, 16, 22, 42, 44, 46, an others, such as fleet data acquired from a fleet of turbomachinery 18, from equipment users (e.g., aircraft 104 service companies), and/or equipment manufacturers, may be used to plan (block 152) maintenance and inspection activities, more efficient inspection schedules for machinery, flag certain areas for a more detailed inspection, and so on. The process 150 may then enable the use of a single mode or a multi-modal inspection (block 154) of desired facilities and equipment (e.g., turbomachinery 18). As mentioned above, the inspection (block 154) may use any one or more of the NDT inspection devices 12 (e.g., borescope 14, PTZ camera 16, eddy current inspection device 92, ultrasonic flaw detector 94, digital radiography device 96), thus providing with one or more modes of inspection (e.g., visual, ultrasonic, eddy current, x-ray). In the depicted embodiment, the mobile device 22 may be used to remote control the NDT inspection devices 12, to analyze data communicated by the NDT inspection devices 12, to provide for additional functionality not included in the NDT inspection devices 12 as described in more detail herein, to record data from the NDT inspection devices 12, and to guide the inspection (block 154), for example, by using menu-driven inspection (MDI) techniques, among others.

Results of the inspection (block 154), may then be analyzed (block 156), for example, by using the NDT device 12, by transmitting inspection data to the cloud 24, by using the mobile device 22, or a combination thereof. The analysis may include engineering analysis useful in determining remaining life for the facilities and/or equipment, wear and tear, corrosion, erosion, and so forth. The analysis may additionally include operations research (OR) analysis used to provide for more efficient parts replacement schedules, maintenance schedules, equipment utilization schedules, personnel usage schedules, new inspection schedules, and so on. The analysis (block 156) may then be reported (block 158), resulting in one or more reports 159, including reports created in or by using the cloud 24, detailing the inspection and analysis performed and results obtained. The reports 159 may then be shared (block 160), for example, by using the cloud 24, the mobile device 22, and other techniques, such as workflow sharing techniques. In one embodiment, the process 150 may be iterative, thus, the process 150 may iterate back to planning (block 152) after the sharing (block 160) of the reports 159. By providing for embodiments useful in using the devices (e.g., 12, 14, 16, 22, 92, 94, 96) described herein to plan, inspect, analyze, report, and share data, the techniques described herein may enable a more efficient inspection and maintenance of the facilities 20, 106 and the equipment 18, 104. Indeed, the transfer of multiple categories of data may be provided, as described in more detail below with respect to FIG. 6.

Figure 6:
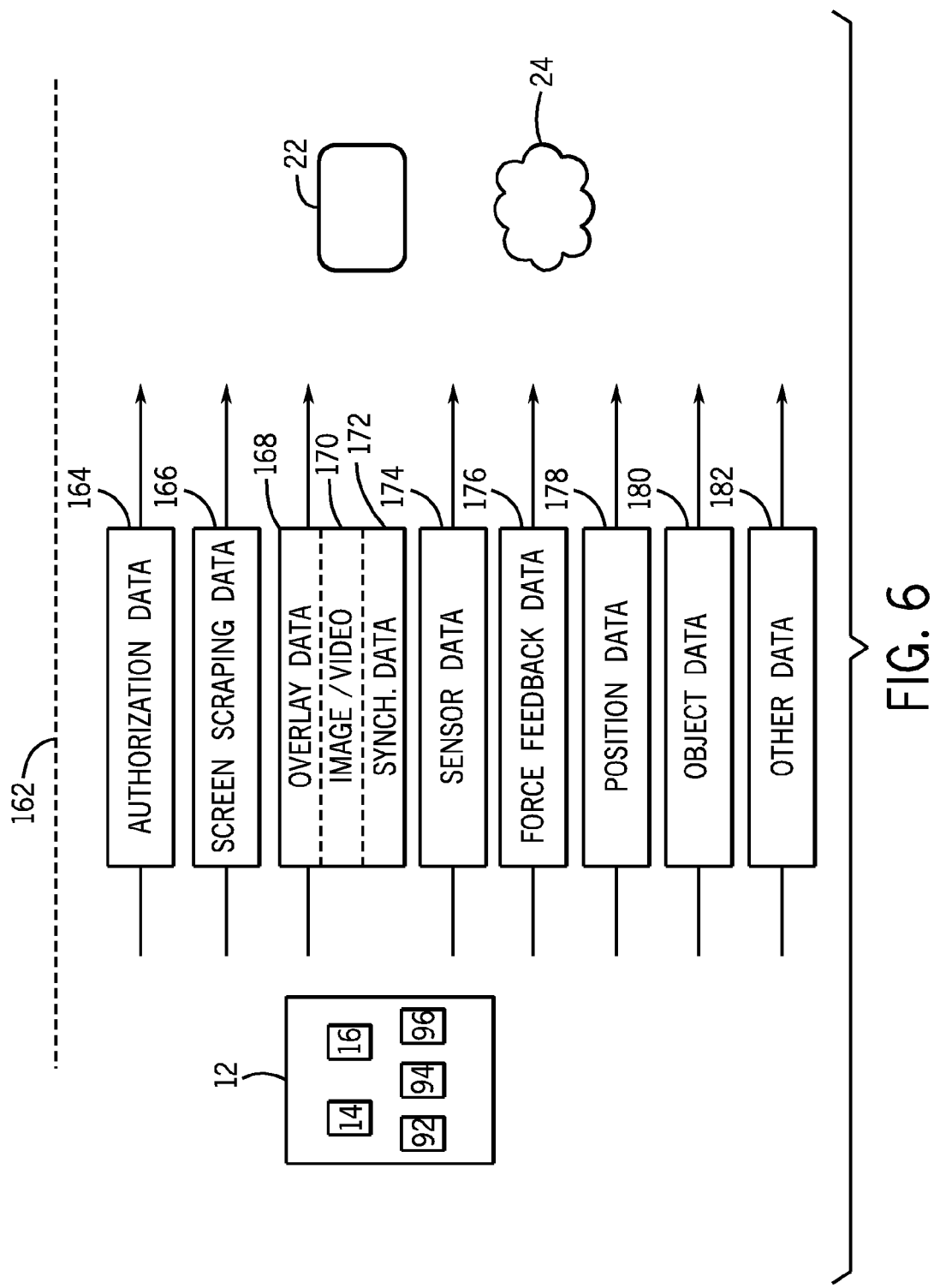
FIG. 6 is a block diagram of an embodiment of information flow through a wireless conduit.

FIG. 6 is a data flow diagram depicting an embodiment of the flow of various data categories originating from the NDT inspection devices 12 (e.g., devices 14, 16, 92, 94, 96) and transmitted to the mobile device 22 and/or the cloud 24. As mentioned above, the NDT inspection devices 12 may use a wireless conduit 162 to transmit the data. In one embodiment, the wireless conduit 112 may include WiFi (e.g., 802.11X), cellular conduits (e.g., HSPA, HSPA+, LTE, WiMax), NFC, Bluetooth, PANs, and the like. The wireless conduit 162 may use a variety of communication protocols, such as TCP/IP, UDP, SCTP, socket layers, and so on. In certain embodiments, the wireless conduit 162 may include secure layers, such as SSL, VPN layers, encrypted layers, challenge key authentication layers, token authentication layers, and so on. Accordingly, an authorization data 164 may be used to provide any number of authorization or login information suitable to pair or otherwise authenticate the NDT inspection device 12 to the mobile device 22 and/or the cloud 24. Additionally, the wireless conduit 162 may dynamically compress data, depending on, for example, currently available bandwidth and latency. The mobile device 22 may then uncompress and display the data. Compression/decompression techniques may include H.261, H.263, H.264, moving picture experts group (MPEG), MPEG-1, MPEG-2, MPEG-3, MPEG-4, DivX, and so on.

In certain modalities (e.g., visual modalities), images and video may be communicated by using certain of the NDT inspection devices 12. Other modalities may also send video, sensor data, and so on, related to or included in their respective screens. The NDT inspection device 12 may, in addition to capturing images, overlay certain data onto the image, resulting in a more informative view. For example, a borescope tip map may be overlaid on the video, showing an approximation of the disposition of a borescope tip during insertion so as to guide the operator 26 to more accurately position the borescope camera 126. The overlay tip map may include a grid having four quadrants, and the tip 136 disposition may be displayed as dot in any portion or position inside of the four quadrants. A variety of overlays may be provided, as described in more detail below, including measurement overlays, menu overlays, annotation overlays, and object identification overlays. The image and video data, such as the video 84, may then be displayed, with the overlays generally displayed on top of the image and video data.

In one embodiment, the overlays, image, and video data may be "screen scraped" from the screen 135 and communicated as screen scrapping data 166. The screen scrapping data 166 may then be displayed on the mobile device 22 and other display devices communicatively coupled to the cloud 24. Advantageously, the screen scrapping data 166 may be more easily displayed. Indeed, because pixels may include both the image or video and overlays in the same frame, the mobile device 22 may simply display the aforementioned pixels. However, providing the screen scraping data may merge both the images with the overlays, and it may be beneficial to separate the two (or more) data streams. For example, the separate data streams (e.g., image or video stream, overlay stream) may be transmitted approximately simultaneously, thus providing for faster data communications. Additionally, the data streams may be analyzed separately, thus improving data inspection and analysis.

Accordingly, in one embodiment, the image data and overlays may be separated into two or more data streams 168 and 170. The data stream 168 may include only overlays, while the data stream 170 may include images or video. In one embodiment, the images or video 170 may be synchronized with the overlays 168 by using a synchronization signal 172. For example, the synchronization signal may include timing data suitable to match a frame of the data stream 170 with one or more data items included in the overlay stream 168. In yet another embodiment, no synchronization data 172 data may be used. Instead, each frame or image 170 may include a unique ID, and this unique ID may be matched to one or more of the overlay data 168 and used to display the overlay data 168 and the image data 170 together.

The overlay data 168 may include a tip map overlay. For example, a grid having four squares (e.g., quadrant grid) may be displayed, along with a dot or circle representing a tip 136 position. This tip map may thus represent how the tip 136 is being inserted inside of an object. A first quadrant (top right) may represent the tip 136 being inserted into a top right corner looking down axially into the object, a second quadrant (top left) may represent the tip 136 being inserted into a left right corner looking down axially, a third quadrant (bottom left) may represent the tip 136 being inserted into a bottom left corner, and a fourth quadrant (bottom right) may represent the tip 136 being inserted into a bottom right corner. Accordingly, the borescope operator 26 may more easily guide insertion of the tip 136.

The overlay data 168 may also include measurement overlays. For example, measurement such as length, point to line, depth, area, multi-segment line, distance, skew, and circle gauge may be provided by enabling the user to overlay one or more cursor crosses (e.g., "+") on top of an image. In one embodiment a stereo probe measurement tip 136, or a shadow probe measurement tip 136 may be provided, suitable for measurements inside of objects, including stereoscopic measurements and/or by projecting a shadow onto an object. By placing a plurality of cursor icons (e.g., cursor crosses) over an image, the measurements may be derived using stereoscopic techniques. For example, placing two cursors icons may provide for a linear point-to-point measurement (e.g., length). Placing three cursor icons may provide for a perpendicular distance from a point to a line (e.g., point to line). Placing four cursor icons may provide for a perpendicular distance between a surface (derived by using three cursors) and a point (the fourth cursor) above or below the surface (e.g., depth). Placing three or more cursors around a feature or defect may then give an approximate area of the surface contained inside the cursors. Placing three or more cursors may also enable a length of a multi-segment line following each cursor.

Likewise, by projecting a shadow, the measurements may be derived based on illumination and resulting shadows. Accordingly, by positioning the shadow across the measurement area, then placing two cursors as close as possible to the shadow at furthermost points of a desired measurement may result in the derivation of the distance between the points. Placing the shadow across the measurement area, and then placing cursors at edges (e.g., illuminated edges) of the desired measurement area approximately to the center of a horizontal shadow may result in a skew measurement, otherwise defined as a linear (point-to-point) measurement on a surface that is not perpendicular to the probe 14 view. This may be useful when a vertical shadow is not obtainable.

Similarly, positioning a shadow across the measurement area, and then placing one cursor on a raised surface and a second cursor on a recessed surface may result in the derivation of depth, or a distance between a surface and a point above or below the surface. Positioning the shadow near the measurement area, and then placing a circle (e.g., circle cursor of user selectable diameter, also referred to as circle gauge) close to the shadow and over a defect may then derive the approximate diameter, circumference, and/or area of the defect.

Overlay data 168 may also include annotation data. For example, text and graphics (e.g. arrow pointers, crosses, geometric shapes) may be overlaid on top of an image to annotate certain features, such as "surface crack." Additionally, audio may be captured by the NDT inspection device 12, and provided as an audio overlay. For example, a voice annotation, sounds of the equipment undergoing inspection, and so on, may be overlaid on an image or video as audio. The overlay data 168 received by the mobile device 22 and/or cloud 24 may then be rendered by a variety of techniques. For example, HTML5 or other markup languages may be used to display the overlay data 168. In one embodiment, the mobile device 22 and/or cloud 24 may provide for a first user interface different from a second user interface provided by the NDT device 12. Accordingly, the overlay data 168 may be simplified and only send basic information. For example, in the case of the tip map, the overlay data 168 may simply include X and Y data correlative to the location of the tip, and the first user interface may then use the X and Y data to visually display the tip on a grid.

Additionally sensor data 174 may be communicated. For example, data from the sensors 126, 140, and x-ray sensor data, eddy current sensor data, and the like may be communicated. In certain embodiments, the sensor data 174 may be synchronized with the overlay data 168, for example, overlay tip maps may be displayed alongside with temperature information, pressure information, flow information, clearance, and so on. Likewise, the sensor data 174 may be displayed alongside the image or video data 170.

In certain embodiments, force feedback or haptic feedback data 176 may be communicated. The force feedback data 176 may include, for example, data related to the borescope 14 tip 136 abutting or contacting against a structure, vibrations felt by the tip 136 or vibration sensors 126, force related to flows, temperatures, clearances, pressures, and the like. The mobile device 22 may include, for example, a tactile layer having fluid-filled microchannels, which, based on the force feedback data 176, may alter fluid pressure and/or redirect fluid in response. Indeed, the techniques describe herein, may provide for responses actuated by the mobile device 22 suitable for representing sensor data 174 and other data in the conduit 162 as tactile forces.

The NDT devices 12 may additionally communicate position data 178. For example, the position data 178 may include locations of the NDT devices 12 in relation to equipment 18, 104, and/or facilities 20, 106. For example, techniques such as indoor GPS, RFID, triangulation (e.g., WiFi triangulation, radio triangulation) may be used to determine the position 178 of the devices 12. Object data 180 may include data related to the object under inspection. For example, the object data 180 may include identifying information (e.g., serial numbers), observations on equipment condition, annotations (textual annotations, voice annotations), and so on. Other types of data 182 may be used, including but not limited to menu-driven inspection data, which when used, provides a set of pre-defined "tags" that can be applied as text annotations and metadata. These tags may include location information (e.g., $1^{st}$ stage HP compressor) or indications (e.g., foreign object damage) related to the object undergoing inspection. Other data 182 may additionally include remote file system data, in which the mobile device 22 may view and manipulate files and file constructs (e.g., folders, subfolders) of data located in the memory 25 of the NDT inspection device 12. Accordingly, files may be transferred to the mobile device 22 and cloud 24, edited and transferred back into the memory 25. By communicating the data 164-182 to the mobile device 22 and the cloud 24, the techniques described herein may enable a faster and more efficient process 150.

Figure 7:
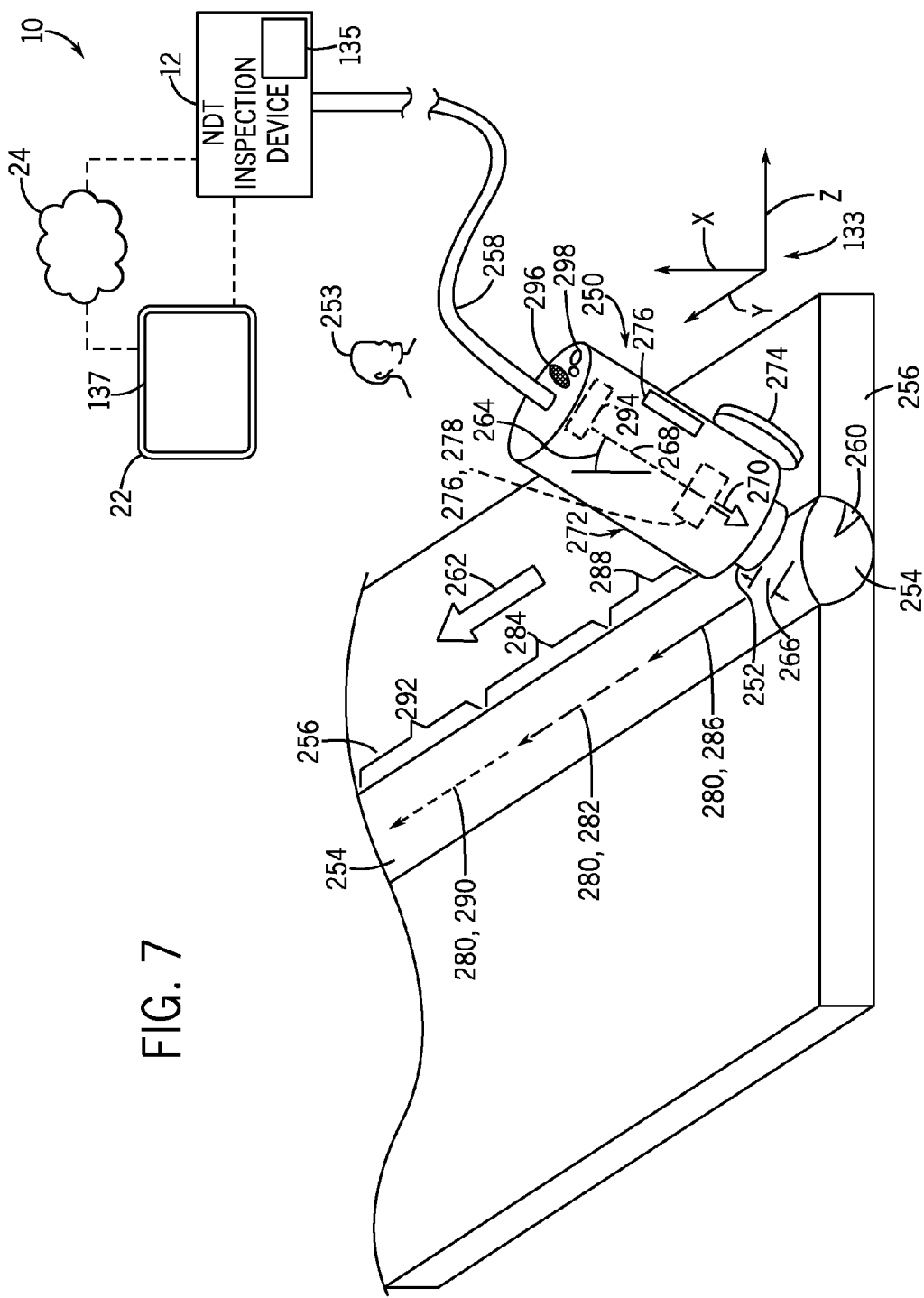
FIG. 7 is a perspective view of an embodiment of an NDT probe of the distributed NDT system of FIG. 1.

FIG. 7 is a perspective view of an embodiment of an NDT probe 250 of the distributed NDT system 10. The NDT probe 250 may include one or more testing sensors 252 associated with the second category of NDT inspection devices 12 (e.g., eddy current inspection device 92, ultrasonic flaw detector 94, digital radiography device 96). Accordingly, the one or more testing sensors 252 may include, but are not limited to eddy current sensors, ultrasonic sensors, x-ray sensors, magnetic field sensors, or light sensors. A probe operator 253 (e.g., eddy current operator 98, ultrasonic device operator 100, radiography operator 102) moves the NDT probe 250 across an inspection area 254 of a workpiece 256. The testing sensors 252 provide the sensor data 174 to the NDT inspection device 12, the mobile device 22, and/or the cloud 24 via a probe cable 258. In some embodiments, the inspection area 254 is a weld, a joint, an area susceptible to high stress and/or fatigue, and so forth. The testing sensor 252 may be used to inspect the workpiece 256 for points of interest 260, such as voids, fissures, cracks, corrosion, etc.

As shown in FIG. 7, the inspection area 254 (e.g., weld) lies parallel to the Y-axis. Accordingly, the probe operator 253 moves the NDT probe 250 along the Y-axis, as shown by the arrow 262, to obtain the sensor data 174. Various spatial factors affect the sensor data 174, including the direction and speed of the NDT probe 250 relative to the workpiece 256, an orientation of the NDT probe 250 relative to the direction of motion 262, an angle 264 of the NDT probe 250 relative to the workpiece 256, and a distance 266 between the NDT probe 250 and the workpiece 256. Additionally, non-spatial factors such as the materials of the workpiece 256 and inspection area 254, the sampling frequency, and/or driving signals supplied to the testing sensor 252, may affect the sensor data 174. The NDT inspection device 12 may be calibrated to process and display sensor data 174 with spatial factors within defined spatial ranges. For example, the NDT inspection device 12 may be calibrated to display sensor data 174 obtained when the NDT probe 250 is moved between approximately 2 to 4 cm/s along the inspection area 254. In some embodiments, the NDT inspection device 12 may be calibrated to display sensor data obtained when an angle 264 between a probe axis 268 of the NDT probe 250 and the X-axis is less than approximately 10 degrees, where the X-axis is perpendicular to the inspection area 254.

Embodiments of the distributed NDT system 10 and the NDT probe 250 may enable the probe operator 253 to obtain consistent sensor data 174. Features of the NDT probe 250 and/or feedback provided to the operator may increase NDT inspection productivity of the probe operator 253, and may increase the probability of detection of points of interest 260 in the inspection area 254. In some embodiments, the NDT probe 250 has an orientation feature 270 (e.g., arrow, ridge, groove) to enable the probe operator 253 to move the NDT probe 250 relative to the workpiece 256 repeatedly with substantially the same orientation. For example, FIG. 7 illustrates the orientation feature 270 on a surface 272 of the NDT probe 250 along the probe axis 268. In some embodiments, the probe operator 253 may align the orientation feature 270 parallel or perpendicular with the direction of motion 262. In this way, the orientation feature 270 may enable the probe operator 253 to maintain a consistent orientation of the NDT probe 250 about the X-axis over multiple NDT inspections.

In some embodiments, a spacer 274 (e.g., wheel, wedge, bumper, ridge) may interface with the workpiece 256 to enable the probe operator 253 to maintain a consistent distance 266 between the NDT probe 250 and the inspection area 254. The orientation feature 270 and the spacer 274 may be passive components that may enable the probe operator 253 to obtain consistent NDT inspection results of the inspection area 254.

One or more motion sensors 276 provide motion data of the NDT probe 250 to the distributed NDT system 10. The one or more motion sensors 276 may transmit motion data along the probe cable 258 to a processor (e.g., mobile device processor 23, NDT inspection device processor 93, 97, 99). A motion sensor 276 may transmit motion data (e.g., position data 178) to indicate changes in the position and/or orientation of the NDT probe 250 relative to the workpiece 256 or coordinate axes 133. The one or more motion sensors 276 may include, but are not limited to, an accelerometer, a gyroscope, a magnetometer, a light sensor, a counter, e.g., coupled to the spacer 274 as it rotates, or any combination thereof. For example, a motion sensor 276 may be an inertial measurement unit (IMU) 278 with a gyroscope and an accelerometer. In some embodiments, the IMU 278 may include a magnetometer. The IMU 278 may transmit motion data corresponding to acceleration motion along and/or rotation about one or more of the coordinate axes 133. In some embodiments, the one or more motion sensors 276 are integrated with the testing sensors 252. For example, the processor 93 may determine the speed of the NDT probe 250 from the sensor data 174. The one or more motion sensors 276 may be arranged within the NDT probe 250 (e.g., along the probe axis 268) and/or on the surface 272 of the NDT probe 250.

The motion sensors 276 detect the movement of the NDT probe 250 in direction 262 along the inspection area 254. The arrows 280 show different speeds at which the NDT probe 250 moves along the inspection area 254. The lined arrow 282 indicates motion of the NDT probe 250 along a first region 284 of the inspection area 254 at a desired speed that is within a reference speed range (e.g., between approximately 2 to 4 cm/s). Accordingly, the NDT inspection device 12 may record the sensor data 174 obtained by the NDT probe 250 for the first region 284. The solid arrow 286 indicates motion of the NDT probe 250 along a second region 288 of the inspection area 254 at a speed (e.g., 5 cm/s) that exceeds (i.e., is outside) the reference speed range. The dotted arrow 290 indicates motion of the NDT probe 250 along a third region 292 of the inspection area 254 at a speed (e.g., 1 cm/s) that is less than (i.e., is outside) the reference speed range. In some embodiments, the NDT inspection device 12 disregards the sensor data 174 from the second region 288 and the third region 292. Alternatively, the NDT inspection device 12 records the sensor data 174 from the second region 288 and the third region 292 with an indicator to note that speed of the NDT probe 250 was outside the reference speed range.

The distributed NDT system 10 may utilize the motion data to provide feedback to the probe operator 253. The feedback may notify the probe operator 253 of spatial factors that affect the sensor data 174, such as the speed, the position, the angle 264, the orientation of the NDT probe 250 relative to the workpiece 256, and the spacing 266 of the NDT probe 250 from the workpiece 256. Using the feedback, the probe operator 253 may adjust the NDT probe 250 on subsequent inspections to produce desirable sensor data 174 results, such as sensor data 174 that is obtained while the spatial factors are within one or more reference ranges. The feedback may enable the probe operator 253 to improve the quality and consistency of the sensor data 174 by adjusting the position, movement, and/or orientation of the NDT probe 250. In some embodiments, the distributed NDT system 10 provides feedback while the probe operator 253 is performing the NDT inspection. In some embodiments, the distributed NDT system 10 provides feedback after an inspection period.

The distributed NDT system 10 may provide feedback to the probe operator 253 through the NDT probe 250, the NDT inspection device 12 (e.g., display screen 135), and/or the mobile device 22 (e.g., display screen 137). In some embodiments, the NDT probe 250 provides haptic feedback to the probe operator 253 via a motor 294 offset from the probe axis 268 or other vibrating component. The NDT probe 250 may have a speaker 296 to provide audio feedback, or lights 298 (e.g., light emitting diodes) to provide visual feedback. A processor, such as the processor 15 in the NDT inspection device 12, may control the feedback from the NDT probe 250. The processor 15 may control the motor 294, the speaker 296, and/or the lights 298 to provide feedback when the motion data is outside one or more reference ranges. The reference ranges include, but are not limited to speed ranges (along the axes 133), angle ranges (between the probe axis 268 and the X-axis), position ranges (relative to the workpiece 256), and orientation ranges (about the axes 133).

The reference ranges may be defined based at least in part on operator input, the category and type of NDT inspection device 12, the workpiece 256 material, and properties (e.g., current, voltage, frequency, polarity) of electrical signals provided to the NDT probe 250. For example, the reference speed range of an eddy current sensor 252 may be based at least in part on the conductivity of the workpiece 256, the amperage of the current supplied to a sensing coil, and the frequency of the current supplied to the sensing coil. The probe operator 253 may load a defined set of reference ranges from a memory or input the bounds of the reference ranges into a user interface 300 based on experience or instructions. For example, the probe operator 253 may narrow the reference ranges after becoming familiar with how to obtain consistent inspection results. The user interface 300 may be accessed through the mobile device 22 and/or the NDT inspection device 12.

The processor 15 may vary the feedback to provide feedback regarding distinct reference ranges. For example, haptic and audio feedback may be provided regarding the speed of the NDT probe 250, whereas visual feedback is provided regarding the angle 264 of the NDT probe 250. The NDT probe 250 may vary the duration and/or the intensity of the feedback based at least in part on the degree to which the motion data is outside the one or more reference ranges. Moreover, in some embodiments, the NDT probe 250 provides feedback when the motion data is within a threshold of bounds of one or more reference ranges. For example, the light 298 may emit yellow light when the speed is within a threshold of approximately 10% of the bounds of the speed reference range (e.g., less than approximately 2.2 cm/s, or greater than approximately 3.8 cm/s), and the light 298 may emit red light when the speed is outside the bounds of the speed reference range (e.g., less than approximately 2.0 cm/s, or greater than approximately 4.0 cm/s).

Figure 8:
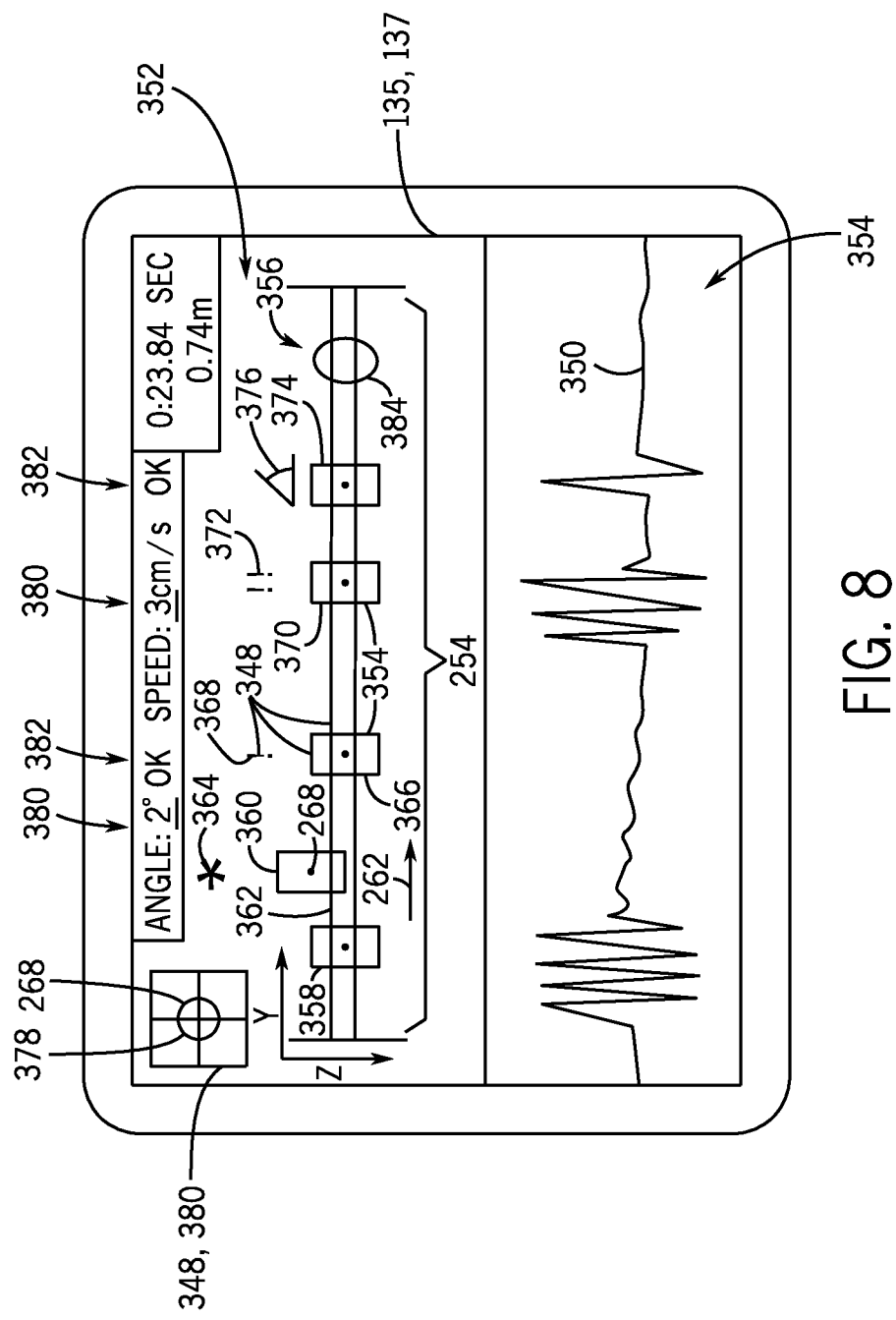
FIG. 8 is a front view of an embodiment of a display screen of the distributed NDT system of FIG. 1 with motion feedback.

The distributed NDT system 10 may provide feedback to the probe operator 253 via one or more display screens 135, 137. FIG. 8 illustrates an embodiment of a display screen 135, 137 of the distributed NDT system 10 with a first graphical representation 348 of motion feedback and a second graphical representation 350 of the sensor data 174. In some embodiments, as shown in FIG. 8, the first graphical representation 348 of the motion feedback 348 is displayed on a first portion 352 of the display screen 137, and the second graphical representation 350 of the sensor data 174 is displayed on a second portion 352. Additionally or alternatively, the first graphical representation 348 may be an overlay over the second graphical representation 350.

A marker 354 in a position chart 356 shows the position of the NDT probe 250 along the Y-axis and the Z-axis as the NDT probe 250 moves in direction 262 along the inspection area 254. Each of the five markers 354 on the position chart 356 show a sample time of the motion data over the inspection area 254. The rate at which the marker 354 moves relative to the position chart 356 provides visual feedback on the speed of the NDT probe 250. A first marker 358 shows that the NDT probe 250 is being moved within the spatial reference ranges. A second marker 360 shows the probe axis 268 outside a reference position range 362 along the Z-axis. A position flag 364 instructs the probe operator 253 to move NDT probe 250 back within the reference position range 362. A third marker 366 is within the reference position range 362, however a slow indicator 368 instructs the probe operator 253 to move the NDT probe 250 more quickly along the inspection area 254. A fourth marker 370 with a fast indicator 372 instructs the probe operator 253 to move the NDT probe 250 more slowly along the inspection area 254.

A fifth marker 374 with an angle indicator 376 shows that the probe axis 268 is near or outside the bounds of a reference angle range 378 as shown in an angle chart 380. The angle chart 380 shows a graphical representation of the NDT probe 250 along the X-axis. The angle indictor 376 instructs the probe operator 253 to move the probe axis 268 within the reference angle range 378. The display screen 137 may show some motion values 380 during the inspection period, such as the angle 264, the speed, the inspected distance, and so forth. In some embodiments, the display screen 137 may have text 382 (e.g., OK, HIGH, LOW, etc.) that indicates whether a motion value is within or outside of the respective reference range.

As may be appreciated, embodiments of the first graphical representation 348 are not limited to the position chart 356, angle chart 380, marker 354, indicators, and text shown in FIG. 8. Various other indicators and charts may provide visual feedback to the probe operator 253 about the speed, position, and orientation of the NDT probe 250 relative to the workpiece 256. In some embodiments, a guide marker 384 may move relative to the position chart 356 at a speed to instruct the probe operator 253 how to move the NDT probe 250. Accordingly, the probe operator 253 moves the NDT probe 250 along the inspection area 254 at a speed within the reference speed range if the relative movement of the marker 354 on the position chart 356 approximately matches the relative movement of the guide marker 384. Guided and/or interactive visual feedback may improve the consistency of sensor data 174 from different probe operators 253, decrease training time of probe operators 253, and/or increase the accuracy of NDT inspections in detecting points of interest 260 in the inspection area 254.

Figure 9:
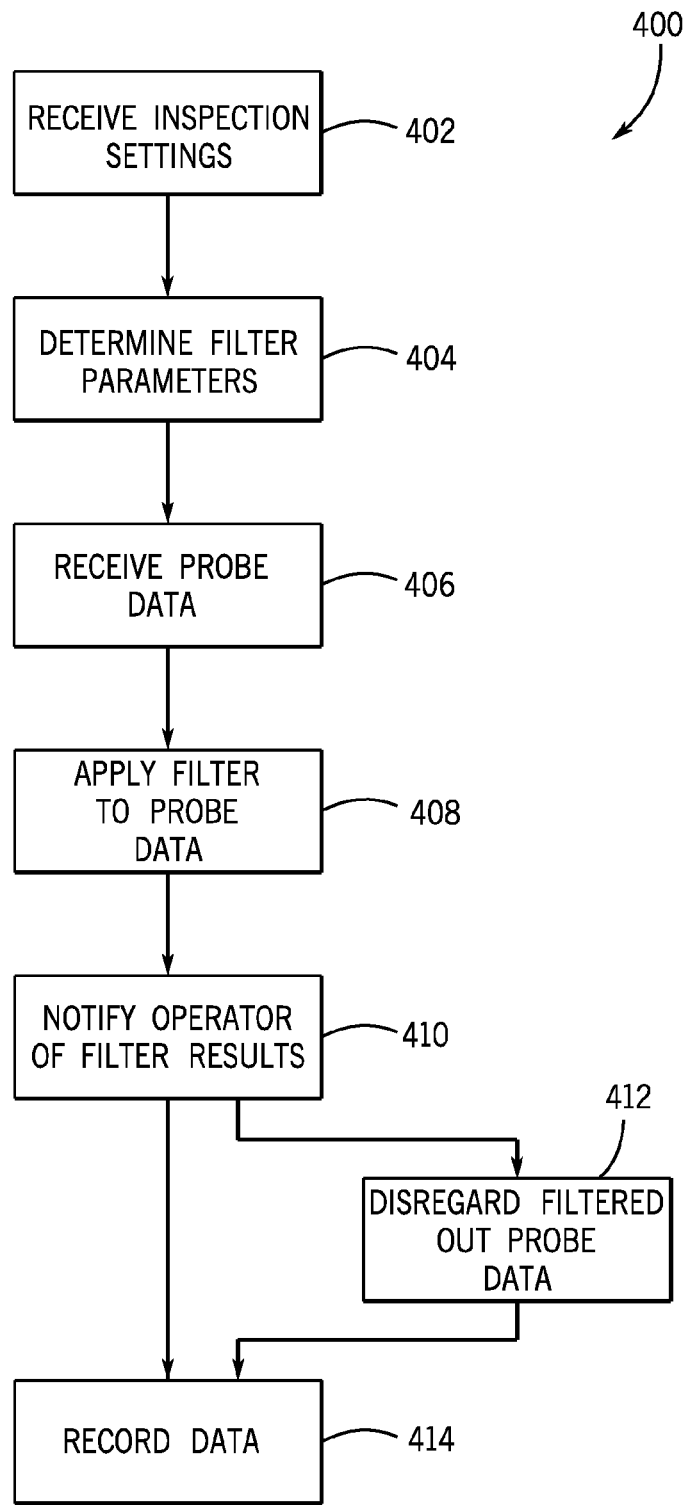
FIG. 9 is a flowchart illustrating an embodiment of a filtering method in the distributed NDT system of FIG. 1 using motion data of the NDT probe.

The first graphical representation 348 is produced by one or more processors of the distributed NDT system 10. The charts, indicators, and text are determined through the motion data, the reference ranges, or comparisons thereof. Probe data from the NDT probe 250 at sample times includes the sensor data 174 and motion data. Sensor data 174 obtained from the NDT probe 250 at sample times corresponding to motion data outside one or more reference ranges may be less valuable and/or less usable than sensor data 174 obtained from the NDT probe 250 at sample times corresponding to motion data within the one or more reference ranges. Accordingly, a filtering method 400 shown in FIG. 9 sorts the sensor data 174 based at least in part on motion data from corresponding sample times.

The filtering method 400 may use the NDT inspection device 12 (e.g., the second category of NDT inspection devices 92, 94, 96) and/or a mobile device 22 to more efficiently support and maintain a variety of equipment. In certain embodiments, the method 400 or portions of the method 400 may be included in non-transitory computer-readable media stored in memory, such as the memory 17, 21, 25, 95, 99, 103 and executable by one or more processors, such as the processors 15, 19, 23, 93, 97, 101.

In one example of the method 400, a processor receives (block 402) inspection settings. The inspection settings may be loaded from the memory 17, 21, 25, 95, 99, 103 or received via the user interface 300. The inspection settings may include the category and type of NDT inspection device 12, the workpiece 256 material, and properties (e.g., current, voltage, frequency, polarity) of electrical signals provided to the NDT probe 250. The processor determines (block 404) parameters of a filter to apply to the probe data based at least in part on the inspection settings. In some embodiments, the processor receives at least some of the bounds of reference ranges directly. The processor receives (block 406) probe data that includes sensor data 174 and motion data for a sample time. In some embodiments, the processor receives (block 406) the probe data for each sample time separately as it is obtained. In other embodiments, the processor receives (block 406) the probe data for multiple sample times of an inspection period after the inspection period has passed.

Once the probe data is received, the processor applies (block 408) the filter to the probe data to sort the sensor data 174 obtained from the NDT probe 250 while the NDT probe 250 was being moved along the inspection area 254 in a desired manner. That is, the sensor data 174 at sample times corresponding to motion data within the one or more reference ranges is separated from the sensor data 174 at sample times corresponding to motion data outside the one or more reference ranges. For example, the processor at block 408 filters out the sensor data 174 from sample times corresponding to when the NDT probe 250 was moved greater than approximately 4 cm/s, at an angle greater than approximately 10 degrees from the X-axis, or not over the inspection area 254. The processor notifies (block 410) the probe operator 253 of the filter results through haptic, audio, and/or visual feedback. The feedback may instruct the probe operator 253 to adjust the motion of the NDT probe 250 so that subsequent sensor data 174 is not filtered out. In some embodiments, the processor may disregard (block 412) the filtered out sensor data 174 and record (block 414) the sensor data 174 corresponding to motion data within the one or more reference ranges (e.g., not filtered out sensor data). Disregarding some of the sensor data 174 generates gaps in the sensor data 174 of the inspection area 254. Accordingly, in some embodiments the processor marks the filtered out sensor data 174 with an indicator to note that the corresponding motion data is outside the one or more motion ranges, and records the sensor data for the inspection area 254.

Technical effects of the invention include providing systems and methods that improve the usability of an NDT device, improve the consistency of inspection results, and improve the accuracy of inspection results. A distributed NDT system is provided, which includes systems and methods of obtaining motion data of the NDT probe 250 and filtering corresponding sensor data 174 based on the motion data. Haptic, audio, and/or visual feedback provided to the probe operator 253 during or after an inspection period enables the operator to adjust the movement of the NDT probe 250 to improve the quality of the inspection results.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal language of the claims.

The invention claimed is:

1. A system comprising:
a non-destructive testing (NDT) system comprising:
an NDT probe comprising a testing sensor, a motion sensor, and a feedback device, wherein the testing sensor is configured to capture sensor data from an inspection area, the motion sensor is configured to detect a measurement speed at which the NDT probe moves relative to the inspection area, and the feedback device is configured to provide an operator-perceptible notification via a haptic feedback, an audio output, or a visual output, or any combination thereof; and
a processor configured to determine a speed comparison between the measurement speed and a reference speed range.

2. The system of claim 1, wherein the processor is configured to disregard the sensor data captured when the measurement speed is outside the reference speed range.

3. The system of claim 1, wherein the feedback device of the NDT probe comprises a haptic device configured to provide haptic feedback to an operator when the measurement speed is outside the reference speed range.

4. The system of claim 1, wherein the feedback device of the NDT probe is configured to provide the audio output or the visual output when the measurement speed is outside the reference speed range.

5. The system of claim 1, wherein the NDT system comprises a display screen configured to visually display the speed comparison.

6. The system of claim 5, wherein the NDT system comprises a mobile device having the display screen.

7. The system of claim 5, wherein the testing sensor comprises an eddy current sensor, an x-ray sensor, an ultrasonic sensor, or a light sensor, or any combination thereof.

8. The system of claim 1, wherein the motion sensor comprises an accelerometer, a gyroscope, a counter, a magnetometer, or any combination thereof.

9. The system of claim 8, wherein the motion sensor is configured to detect a measurement angle of the NDT probe relative to an axis perpendicular to the inspection area, and the processor is configured to determine an angle comparison between the measurement angle and a reference angle range.

10. The system of claim 1, wherein the reference speed range is based at least in part on a user input, the inspection area, or a current use of the NDT probe, or any combination thereof.

11. A non-transitory computer readable medium comprising instructions configured to:
 capture sensor data from an inspection area, by using a non-destructive testing (NDT) probe;
 determine a measurement speed of the NDT probe and a measurement angle of the NDT probe relative to an axis perpendicular to the inspection area;
 determine a speed comparison between the measurement speed and a reference speed range;
 determine an angle comparison between the measurement angle and a reference angle range;
 display a first graphical representation of the speed comparison and a second graphical representation of the angle comparison on a display screen.

12. The non-transitory computer readable medium of claim 11, comprising instructions configured to display a speed warning on the display screen when the speed comparison is within a speed threshold of speed bounds of the reference speed range, or to display an angle warning on the display screen when the angle comparison is within an angle threshold of angle bounds of the reference angle range, or any combination thereof.

13. The non-transitory computer readable medium of claim 11, comprising instructions configured to:
 receive a user input by using a user interface; and
 determine the reference speed range and the reference angle range based at least in part on the user input.

14. The non-transitory computer readable medium of claim 11, comprising instructions configured to display on the display screen a speed guide, an angle guide, or any combination thereof.

15. The non-transitory computer readable medium of claim 11, comprising instruction configured to:
 classify the sensor data based on the speed comparison and the angle comparison corresponding to a time the sensor data is captured;
 recording the sensor data in a memory.

16. A method comprising:
 receiving probe data from a non-destructive testing (NDT) device, wherein the probe data comprises sensor data and motion data, wherein the sensor data and motion data correspond to a sample time;
 comparing the motion data to one or more motion reference ranges;
 displaying a position marker and a guide marker on a display screen, wherein the position marker corresponds to the motion data, and relative movement of the guide marker on the display screen corresponds to the one or more reference ranges;
 notifying an operator if the motion data of the sample time is outside the one or more motion reference ranges; and
 recording the sensor data of the sample time if the motion data of the sample time is within the one or more motion reference ranges.

17. The method of claim 16, wherein the one or more reference ranges comprise a speed range of the NDT device relative to an inspection area, an angle range of the NDT device relative to an axis perpendicular to the inspection area, or any combination thereof.

18. The method of claim 16, wherein notifying the operator comprises providing haptic feedback, audio feedback, or visual feedback to the operator.

19. The method of claim 16, comprising notifying the operator if the motion data of the sample time is within a threshold of bounds of the one or more reference ranges.

20. The method of claim 16, comprising recording the sensor data of the sample time if the motion data of the sample time is outside the one or more motion reference ranges, wherein the sensor data comprises an indicator that the motion data is outside the one or more motion reference ranges.

* * * * *

UNITED STATES PATENT AND TRADEMARK OFFICE
CERTIFICATE OF CORRECTION

PATENT NO. : 9,003,880 B2
APPLICATION NO. : 13/732268
DATED : April 14, 2015
INVENTOR(S) : Sbihli et al.

Page 1 of 1

It is certified that error appears in the above-identified patent and that said Letters Patent is hereby corrected as shown below:

On the Title Page, in Item (52), under "U.S. Cl.", in Column 1, Line 7, insert
-- USPC......73/488; 73/639 --, therefor.

Specification

In Column 5, Line 20, delete "operator 28" and insert -- operator 28, --, therefor.

In Column 6, Line 23, delete "wheels 50" and insert -- wheels 50, --, therefor.

In Column 6, Line 65, delete "memory 104." and insert -- memory 103. --, therefor.

In Column 7, Line 16, delete "analsysis." and insert -- analysis. --, therefor.

In Column 7, Lines 41-42, delete "boresecope" and insert -- borescope --, therefor.

In Column 8, Line 8, delete "plane X-Z" and insert -- plane, X-Z --, therefor.

In Column 9, Line 15, delete "140 data," and insert -- data 140, --, therefor.

In Column 10, Line 64, delete "video 84," and insert -- video 134, --, therefor.

In Column 14, Line 31, delete "97, 99" and insert -- 97, 101 --, therefor.

In Column 16, Line 17, delete "feedback 348" and insert -- feedback --, therefor.

Signed and Sealed this
Twenty-fourth Day of November, 2015

Michelle K. Lee
*Director of the United States Patent and Trademark Office*